United States Patent
Lee et al.

(10) Patent No.: US 10,512,635 B2
(45) Date of Patent: Dec. 24, 2019

(54) USES OF BENZIMIDAZOLE DERIVATIVE FOR NOCTURNAL ACID BREAKTHROUGH

(71) Applicants: CJ HEALTHCARE CORPORATION, Seoul (KR); RaQualia Pharma Inc., Aichi (JP)

(72) Inventors: Ha Jin Lee, Seoul (KR); Bong Tae Kim, Gyeonggi-do (KR); Hyun Kim, Gyeonggi-do (KR); Ji Yeon Nam, Seoul (KR); Jie Eun Park, Gyeonggi-do (KR); Geun Seog Song, Seoul (KR); Shin Young Ryu, Gyeonggi-do (KR); Shinichi Koizumi, Aichi (JP); Nobuyuki Takahashi, Aichi (JP); Masaomi Tajimi, Aichi (JP)

(73) Assignees: CJ Healthcare Corporation, Seoul (KR); RaQualia Pharma Inc., Aichi (JP)

(*) Notice: Subject to any disclaimer, the term of this patent is extended or adjusted under 35 U.S.C. 154(b) by 0 days.

(21) Appl. No.: 15/580,850

(22) PCT Filed: Jun. 8, 2016

(86) PCT No.: PCT/KR2016/006072
§ 371 (c)(1),
(2) Date: Dec. 8, 2017

(87) PCT Pub. No.: WO2016/200148
PCT Pub. Date: Dec. 15, 2016

(65) Prior Publication Data
US 2018/0338954 A1    Nov. 29, 2018

Related U.S. Application Data
(60) Provisional application No. 62/172,680, filed on Jun. 8, 2015.

(51) Int. Cl.
*A61K 31/4184* (2006.01)
*A61K 9/20* (2006.01)
(Continued)

(52) U.S. Cl.
CPC ............ *A61K 31/4184* (2013.01); *A61K 9/20* (2013.01); *A61K 9/28* (2013.01); *A61P 1/04* (2018.01)

(58) Field of Classification Search
CPC .............................. A61K 31/44; A61K 31/497
See application file for complete search history.

(56) References Cited

U.S. PATENT DOCUMENTS 7,718,809 B2   5/2010   Koike et al.
7,723,321 B2   5/2010   Hanazawa et al.
(Continued)

FOREIGN PATENT DOCUMENTS

EP   1 963 311     6/2010
KR   2012-0052269  5/2012
(Continued)

OTHER PUBLICATIONS

Tutuian et al., Medscape General Medicine, 2004;6(4):11 (Year: 2004).*

(Continued)

*Primary Examiner* — San Ming R Hui
(74) *Attorney, Agent, or Firm* — Wenderoth, Lind & Ponack, L.L.P.

(57) ABSTRACT

The present invention relates to a use of benzimidazole derivative compounds for improvement and treatment of nocturnal acid breakthrough (NAB). The benzimidazole derivative compounds can mere effectively prevent and treat gastric acid-related diseases by effectively improving and treating nocturnal nocturnal acid breakthrough symptoms.

13 Claims, 1 Drawing Sheet

(51) Int. Cl.
  *A61K 9/28* (2006.01)
  *A61P 1/04* (2006.01)

(56) References Cited

U.S. PATENT DOCUMENTS

| 8,648,080 | B2* | 2/2014 | Takahashi | A61K 31/4184 |
| | | | | 514/252.13 |
| 2005/0232992 | A1* | 10/2005 | Devane | A61K 9/1676 |
| | | | | 424/468 |
| 2007/0142448 | A1 | 6/2007 | Hanazawa et al. | |
| 2008/0214519 | A1 | 9/2008 | Koike et al. | |
| 2012/0115820 | A1 | 5/2012 | Takahashi et al. | |
| 2014/0271853 | A1 | 9/2014 | Hall et al. | |

FOREIGN PATENT DOCUMENTS

| WO | 2006-134460 | 12/2006 |
| WO | 2007-072146 | 6/2007 |
| WO | 2008-151927 | 12/2008 |
| WO | 2009/113696 | 9/2009 |
| WO | 2011-004882 | 1/2011 |
| WO | 2011/095057 | 8/2011 |

OTHER PUBLICATIONS

International Search Report dated Oct. 10, 2016 in International Application No. PCT/KR2016/006072.
Korean Office Action dated Mar. 27, 2019 in corresponding Korean Application No. 10-2018-0034581 with English language translation.
Hee Youn Choi, "Population Pharmacokinetics and Pharmacodynamics of CJ-12420, a Novel Potassium-competitive Acid Blockers (P-CAB) in Healthy Adult Volunteers", Dissertation submitted to The Graduate School of the University of Ulsan Department of Medicine, Feb. 2015, for Doctor of Philosophy.
Office Action dated Jul. 8, 2018 in corresponding Moroccan Patent Application No. 41730 with English translation.
Extended European Search Report dated Dec. 21, 2018 in corresponding European Patent Application No. 16807788.1.
Skrzydlo-Radomańska et al., "Dexlansoprazole—a new-generation proton pump inhibitor", Gastroenterology Review, vol. 10, No. 4, pp. 191-196 (Jan. 1, 2015).

* cited by examiner

USES OF BENZIMIDAZOLE DERIVATIVE FOR NOCTURNAL ACID BREAKTHROUGH

TECHNICAL FIELD

The present disclosure relates to a use of benzimidazole derivative compounds for improvement and treatment of nocturnal acid breakthrough (NAB).

BACKGROUND ART

Up to now, in the treatment of gastroesophageal re-flux disease (GERD), proton pump inhibitors (PPI) have been practically used as standard therapy, and histamine H2-receptor antagonists and antacids have been used as auxiliary/complementary drugs thereof.

Among gastroesophageal reflux disease patients, a standard dose of PPI is generally prescribed for erosive gastroesophageal reflux disease patients, and a half of standard dose is prescribed for non-erosive gastroesophageal reflux disease patients. However, 20 to 30% of patients taking a daily standard dose of PPI do not obtain a sufficient effect in the treatment of gastroesophageal reflux disease, and are suffering the pains caused by nocturnal acid breakthrough (NAB). In this case, depending on treatment guidelines, it is recommended to take a half of standard dose of PPI twice in a day or increase the dose of PPI two times.

Particularly, although about 60 to 70% of gastroesophageal reflux disease patients take PPI, they are suffering the heartburn caused by the sudden drop in gastric pH at dawn according to the occurrence of nocturnal acid breakthrough (NAB). Thus, there is a problem in that gastroesophageal reflux disease recurs, and night sleep is hindered, so as to significantly deteriorate the overall life quality. Further, nocturnal acid breakthrough is a target to be overcome in that it causes pains to the patients suffering Barrett's esophagus and esophagus motility disorder as well as GERD.

Meanwhile, dexlansoprazole, which is a recently launched new-type second generation PPI, is known as a PPI most effective in suppressing nocturnal acid breakthrough.

DISCLOSURE

Technical Problem

Accordingly, the present inventors had made strenuous efforts to find a material having an excellent effect, compared to conventional dexlansoprazole, while remarkably suppressing a nocturnal acid breakthrough phenomenon occurring even after taking a PPI. As a result, they first found that specific benzimidazole derivative compounds have an excellent nocturnal acid breakthrough suppressing effect compared to conventional therapeutic drugs, such as dexlansoprazole. Based on this finding, the present invention has been completed.

Technical Solution

In order to accomplish the above objects, an aspect of the present invention is to provide a pharmaceutical composition for prevention or treatment of nocturnal acid breakthrough, including: a compound represented by Chemical Formula 1 below or a pharmaceutically acceptable salt thereof, as an active ingredient.

[Chemical Formula 1]

Another aspect of the present invention is to provide a unit dosage form for prevention or treatment of nocturnal acid breakthrough, including: 50 mg to 200 mg of the compound represented by Chemical Formula 1 above or the pharmaceutically acceptable salt thereof.

Effects of the Invention

The compound of the present disclosure can more effectively prevent and treat a gastroesophageal reflux disease by effectively preventing and treating nocturnal acid breakthrough accompanying the administration of a proton pump inhibitor.

Further, it is confirmed that the effects thereof last for a long time. Thus, there is an advantage in that the convenience of taking drugs is remarkably high because sufficient effects can be exhibited by the administration of the compound once a day without additionally administering the compound at dawn.

BEST MODE FOR INVENTION

An aspect of the present disclosure provides a pharmaceutical composition for prevention or treatment of nocturnal acid breakthrough, including: a compound represented by Chemical Formula 1 below or a pharmaceutically acceptable salt thereof, as an active ingredient.

Another aspect of the present disclosure provides a unit dosage form for prevention or treatment of nocturnal acid breakthrough, including: 50 mg to 200 mg of a compound represented by Chemical Formula 1 below or a pharmaceutically acceptable salt thereof.

[Chemical Formula 1]

The compound represented by Chemical Formula 1 above is also referred to as "4-(5,7-difluorochroman-4-yloxy)-N,N,2-trimethyl-1H-benzo[d]imidazole-6-carboxamide".

The compound may be isolated from a natural source, may be prepared by chemically modifying or reforming the product obtained from the natural source, or may be prepared by chemical synthesis according to the synthesis method (International Patent Publication WO 2007/072146) known to those skilled in the art. Alternatively, the compound can be commercially available one.

The compound represented by Chemical Formula 1 above according to the present disclosure includes not only the compound or the pharmaceutically acceptable salt thereof but also all solvates, hydrates and stereoisomers being able to be prepared therefrom and exhibiting the same efficacy within the scope of the present disclosure.

The pharmaceutical composition of the present disclosure may include the compound represented by Chemical Formula 1 above or the pharmaceutically acceptable salt thereof in an amount of 10 mg to 500 mg, specifically, in an amount of 50 mg to 200 mg, but is not limited thereto.

In the present disclosure, the "pharmaceutically acceptable salt" refers to a salt formed by reacting with any inorganic acid, organic acid or base, which do not cause severe stimuli to an organism to be administered and do not deteriorate the biological activity and physical properties of the compound. As the salt, salts as commonly used in the art, such as acid addition salts formed by pharmaceutically acceptable free acids, may be used.

In the present disclosure, the "prevention" includes all actions for suppressing or retarding the occurrence of nocturnal acid breakthrough (NAB) or gastric acid-related diseases, such as erosive gastroesophageal reflux disease, non-erosive gastroesophageal reflux disease (NERD), and gastric ulcer by administering the composition or unit dosage form of the present disclosure, and the "treatment" includes all actions for improving or ameliorating the symptoms of nocturnal acid breakthrough or gastric acid-related diseases by using the composition or unit dosage form of the present disclosure.

In the present disclosure, the "nocturnal acid breakthrough (NAB)" is a disease or symptom found in the patients who take a proton pump inhibitor, and particularly refers to a phenomenon in which gastric acid is refluxed at night-time. Generally, the nocturnal acid breakthrough (NAB) is defined as a case where gastric pH is maintained at lower than 4, for duration of 1 hour or more at night-time. Heartburn may be caused due to a sudden drop of gastric pH at dawn by the nocturnal acid breakthrough. Thus, gastric acid-related diseases, such as gastroesophageal reflux disease, rather recur, causing a severe problem of hindering sleep at night. However, therapeutic agents capable of solving nocturnal acid breakthrough symptoms accompanied by the administration of PPI have not been developed.

In the present disclosure, the "gastric acid-related diseases" include disorders or diseases that can occur in a gastroesophageal region by gastric acid or the likes, and non-limiting examples thereof may include erosive gastroesophageal reflux disease (GERD), non-erosive gastroesophageal reflux disease (NERD), gastric ulcer, Barret's esophagus, and esophagus motility disorder.

The compound represented by Chemical Formula 1 above according to the present disclosure acts as a proton pump inhibitor to have not only an effect of treating and improving gastric acid-related diseases but also an effect of preventing the recurrence of gastric acid-related diseases by suppressing the accompanied nocturnal acid breakthrough.

Specifically, the compound represented by Chemical Formula 1 above according to the present disclosure is configured such that the percentage of time when gastric pH is maintained above 4 out of 24 hours after the administration of the compound is 50% or more, specifically 70% or more, and more specifically 80% or more. Therefore, it was ascertained that the compound represented by Chemical Formula 1 maintains the gastric pH value at a high pH stage for a relatively long period of time.

Particularly, (i) the percentage of time when gastric pH is maintained above 4 was calculated to be 60% or more, specifically 65% or more, more specifically 70% or more, and still more specifically 75%, for the first 12 hours after the administration of the compound (night-time 12 hours), and (ii) the percentage of time when gastric pH is maintained above 4 to be 50% or more, specifically 70% or more, and more specifically 85% or more, for 12-24 hours after the administration of the compound (day-time 12 hours)

Further, it was ascertained that the compound represented by Chemical Formula 1 above according to the present disclosure increases the gastric pH to 4 or higher within 2 hours after the administration of the compound.

The pharmaceutical composition or unit dosage form including the compound represented by Chemical Formula 1 above or the pharmaceutically acceptable salt may further include a generally used carrier, excipient or diluent.

In the present disclosure, the "pharmaceutically acceptable carrier" includes carriers or diluents not deteriorating the biological activity and physical properties of the injected compound while not stimulating organisms. The kind of carrier that can be used in the present disclosure is not particularly limited, and any carrier may be used as long as it is generally used in the art and is pharmaceutically acceptable. Non-limiting examples of the carrier may include saline, sterile water, a Ringer's solution, buffered saline, an albumin injection solution, a dextrose solution, a maltodextrin solution, glycerol, and ethanol. They may be used independently or in the form of a mixture of two or more. Further, if necessary, the carrier may also be used together with other general additives, such as an antioxidant, a buffer solution and/or a bacteriostatic agent.

The content of the compound represented by Chemical Formula 1 or the pharmaceutically acceptable salt thereof is not particularly limited, but may be 0.01 wt % to 50.0 wt %, specifically, 0.1 wt % to 10.0 wt %, with respect to the total weight of the composition or the unit dosage form.

Further, the present disclosure provides a method of preventing or treating nocturnal acid breakthrough or gastric acid-related diseases, including the step of administering the pharmaceutical composition or the unit dosage form into a subject.

The pharmaceutical composition or the unit dosage form may be administered into a suspicious subject in a pharmaceutically effective amount for the purpose of prevention or treatment of nocturnal acid breakthrough or gastric acid-related diseases. The pharmaceutical composition or the unit dosage form may be administered independently, or may be used in combination with surgery, radiation therapy, hormone therapy, chemical therapy, and biological response modifier therapy.

In the present disclosure, the types of suspicious subject are not particularly limiting, and any subject may be applied as long as it indicates a nocturnal acid breakthrough symptom, and, particularly, generated or can generate gastric acid-related diseases. Specific examples of the subject may include non-human animals, such as monkeys, dogs, cats, rabbits, marmots, rats, mice, cows, sheep, pigs and goats, and humans. The subject can be efficiently treated by administering the pharmaceutical composition or unit dosage form including the compound of the present disclosure or the pharmaceutically acceptable salt thereof into a suspicious subject.

In the present disclosure, the "administration" refers to a case of injecting the pharmaceutical composition or unit dosage form of the present disclosure into a suspicious subject in any suitable manner. The pharmaceutical composition or unit dosage form of the present disclosure may be administered through various oral or parenteral administration routes through which the pharmaceutical composition or the unit dosage form can reach target tissues. Specifically, the pharmaceutical composition or unit dosage form of the present disclosure may be administered by an oral administration method, but the present disclosure is not limited thereto.

The present disclosure provides a use of the compound represented by Chemical Formula 1 or the pharmaceutically acceptable salt thereof for preparing a pharmaceutical composition, an unit dosage form or a medicament for prevention, treatment or improvement of nocturnal acid breakthrough or gastric acid-related diseases.

Mode for Invention

Hereinafter, the present invention will be described in more detail with reference to the following Examples. These Examples are set forth to illustrate the present disclosure, and the scope of the present disclosure is not limited thereto.

Example 1: Preparation of Pharmaceutical Formulation (1): CJ-12420 50 mg

A formulation containing 50 mg of 4-[(5,7-difluoro-3,4-dihydro-2H-chromen-4-yl)oxy]-N,N,2-trimethyl-1H-benzimidazole-6-carboxamide as a main ingredient was prepared. In the preparation of the formulation, mannitol, macrocrystalline cellulose, and sodium crosscarmellose were mixed with the main ingredient, fillers being contained in a ratio of 1% to 99% (mannitol 50 mg, microcrystalline cellulose 80 mg) with respect to parts by weight of the final formulation, and a disintegrant was used within a range of 1% to 20% (sodium crosscarmellose 10 mg) with respect to parts by weight of the final formulation.

A binding solution containing hydroxypropyl cellulose and purified water was added to this mixture to granulate the mixture, so as to obtain granules. A binder was used within a range of 4% to 40% (hydroxypropyl cellulose 6 mg) with respect to parts by weight of an active ingredient.

The granules were dried and then milled. The milled granules were mixed with macrocrystalline cellulose, sodium crosscarmellose, colloidal silicon dioxide, and magnesium stearate.

A diluent was used within a range of 1% to 10% (colloidal silicon dioxide 2 mg) with respect to parts by weight of the final formulation, a lubricant was used within a range of 1% to 10% (magnesium stearate 2 mg) with respect to parts by weight of the final formulation, and the resulting mixture was compressed to form a tablet.

The tablet was coated with a film coating agent. The film coating agent was applied in a weight ratio of 2% to 6% (6 mg) with respect to parts by weight of the final formulation.

Example 2: Preparation of Pharmaceutical Formulation (2): CJ-12420 100 mg

A formulation containing 100 mg of 4-[(5,7-difluoro-3,4-dihydro-2H-chromen-4-yl)oxy]-N,N,2-trimethyl-1H-benzimidazole-6-carboxamide as a main ingredient was prepared. In the preparation of the formulation, mannitol, microcrystalline cellulose, and sodium crosscarmellose were mixed with the main ingredient, fillers being contained in a ratio of 1% to 99% (mannitol 100 mg, microcrystalline cellulose 160 mg) with respect to parts by weight of the final formulation, and a disintegrant was used within a range of 1% to 20% (sodium crosscarmellose 20 mg) with respect to parts by weight of the final formulation.

A binding solution containing hydroxypropyl cellulose and purified water was added to this mixture to granulate the mixture, so as to obtain granules. A binder was used within a range of 4% to 40% (hydroxypropyl cellulose 12 mg) with respect to parts by weight of an active ingredient.

The granules were dried and then milled. The milled granules were mixed with microcrystalline cellulose, sodium crosscarmellose, colloidal silicon dioxide, and magnesium stearate.

A diluent was used within a range of 1% to 10% (colloidal silicon dioxide 4 mg) with respect to parts by weight of the final formulation, a lubricant was used within a range of 1% to 10% (magnesium stearate 4 mg) with respect to parts by weight of the final formulation, and the resulting mixture was compressed to form a tablet.

The tablet was coated with a film coating agent. The film coating agent was applied in a weight ratio of 2% to 6% (12 mg) with respect to parts by weight of the final formulation.

Comparative Example: Preparation of Dexlansoprazole Formulation

In the preparation of a dexlansoprazole formulation, Dexilant DP capsules (dexlansoprazole 60 mg) commercially available from Takeda Pharmaceuticals Co., Ltd. was purchased and used.

Experimental Example: Clinical Trial

1. Selection of Trial Subjects

Figure 1:
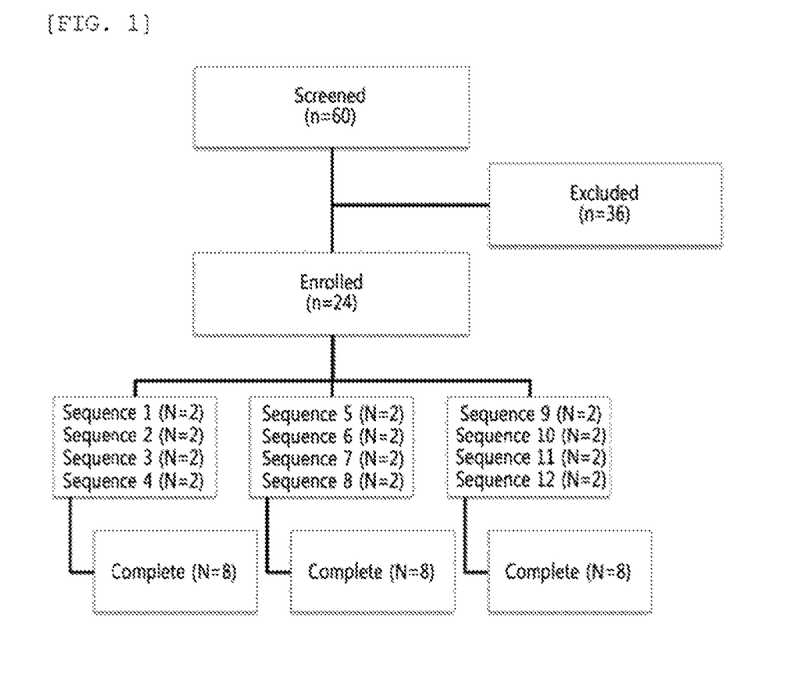
FIG. 1 is a block diagram showing the assignment of subjects in a clinical trial according to the present experimental example.
Figure 2:
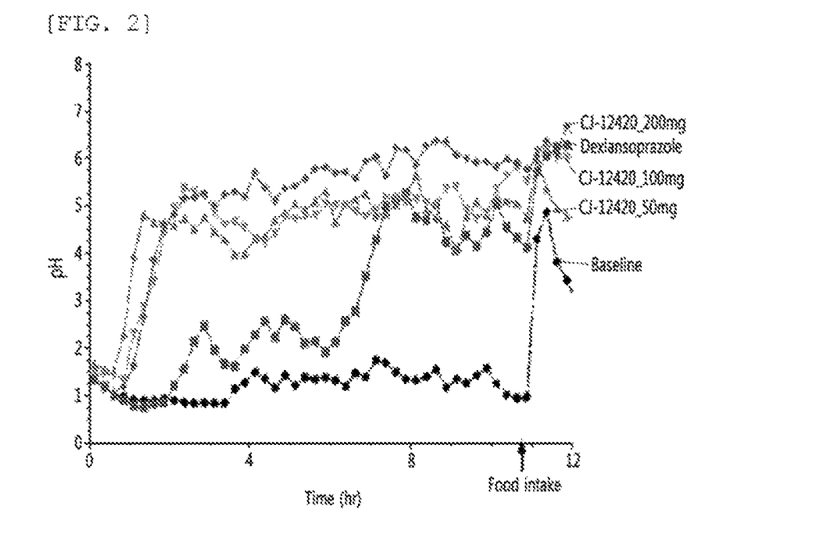
FIG. 2 is a graph showing the gastric pH changes over time in each subject (changes in median values of gastric pH, measured at an average interval of 15 minutes) during night-time, after the administration of the formulations according to the present invention and dexlansoprazole formulation as a control group, into the target subjects at night.

In order to evaluate the nocturnal acid breakthrough inhibiting effect of the compound of Chemical Formula 1 according to the present disclosure, clinical trials were designed by Randomized, Open-label, Single-dose, Balanced incomplete block crossover. A total of 24 trial subjects were enrolled for 12 sequences, with two trial subjects assigned per a sequence. All the trial subjects have completed the planned clinical trial schedule (FIG. 1 and Table 1).

Inclusion Criteria

Trial subjects were required to satisfy all the following selection criteria to participate in this clinical trial, unless otherwise specified.

(1) Healthy male volunteers having an age of 20 to 45 years (2) Persons having a body mass index (EMI) of 19 kg/m² to 28 kg/m² and a body weight of 50 kg or more (3) Medically healthy persons not indicating clinically significant vital signs (blood pressure in the sitting position, pulse rate)

90 mmHg≤systolic blood pressure≤140 mmHg
50 mmHg≤diastolic blood pressure≤95 mmHg
45 (times/min)≤pulse rate≤95 (times/min)

(4) Persons understanding the compliance requirements of this clinical trial and voluntarily agreeing to participate in this clinical trial (5) Persons having agreed to use an effective contraception method and not to provide sperms, for a duration smarting from the day of first trial drug administration ending on 30 days after the last trial drug administration (6) No-smoking persons or persons having quitted smoking for one year or more (7) *H. pylori*-negative persons in Urea Breath Test Exclusion Criteria Persons corresponding to at least one of the following criteria were excluded from this clinical trial.

(1) A person as determined by the investigator to threaten her own safety or to make a negative influence on the validity of clinical trial results due to her clinically significant history of diseases such as digestive system disease, kidney disease, liver disease, nervous system disease, blood tumor system disease, endocrine system disease, respiratory disease, immune system disease, psychiatric disease, musculoskeletal disease, cardiovascular disease, and etc.

(2) A person having a history of allergy or hypersensitivity to drugs including serious abnormal response to gastric acid secretion inhibitors (PPI (omeprazole, rabeprazole, lansoprazole), P-CAB, etc.)

(3) A person having received a surgery influencing the absorption, distribution, metabolism and excretion of medicinal clinical drugs or having been determined to be in such a medical state by the trial investigator or manager (4) A person having been treated with medicinal drugs for other clinical trials within 90 days before screening visit (5) A person having made a whole blood donation within 60 days before screening visit or having made an ingredient blood donation or received a blood transfusion within 30 days before screening visit (6) A person having conducted a special diet or changed eating habits within 30 days before screening visit (7) A person having been treated with expert-the-counter (ETC) drugs within 14 days before screening visit or having been treated with over-the-counter (OTC) drugs including herbal products (oriental drugs) within 7 days before screening visit (8) A person having an alcohol intake of more than 21 units per week (alcohol>21 units/week)

(9) A person having a caffeine-containing beverage intake of more than 5 units per day (caffeine-containing beverage>5 units/day)

(10) A person showing a positive reaction in urine drug screening test or urine nicotine test (11) A person showing a positive reaction for human immunodeficiency virus (HIV), B-type hepatitis, C-type hepatitis, or syphilis (12) A person showing clinically significant abnormal numerical values in liver function test (i.e., the case where each of the numerical values of ALT, AST and total bilirubin is 1.5 times or more the normal upper limit)

(13) A person who cannot withstand the insertion of a pH catheter (14) A person having a history of symptomatic GERD, erosive esophagitis, duodenal ulcer, gastric ulcer, Barrett's esophagus, or Zollinger-Ellison syndrome (15) A person having clinically significant opinion by the investigator that the subject is unsuitable for the clinical trials

TABLE 1

| Group | No. of Subjects administered | Treatment Period 1 | Period 2 |
|---|---|---|---|
| 1 | 2 | Dexlansoprazole 60 mg | COMPOUND I 50 mg |
| 2 | 2 | COMPOUND I 50 mg | COMPOUND I 100 mg |
| 3 | 2 | COMPOUND I 100 mg | COMPOUND I 200 mg |
| 4 | 2 | COMPOUND I 200 mg | Dexlansoprazole 60 mg |
| 5 | 2 | Dexlansoprazole 60 mg | COMPOUND I 100 mg |
| 6 | 2 | COMPOUND I 50 mg | COMPOUND I 200 mg |
| 7 | 2 | COMPOUND I 200 mg | COMPOUND I 50 mg |
| 8 | 2 | COMPOUND I 100 mg | Dexlansoprazole 60 mg |
| 9 | 2 | Dexlansoprazole 60 mg | COMPOUND I 200 mg |
| 10 | 2 | COMPOUND I 200 mg | COMPOUND I 100 mg |
| 11 | 2 | COMPOUND I 100 mg | COMPOUND I 50 mg |
| 12 | 2 | COMPOUND I 50 mg | Dexlansoprazole 60 mg |

In Table 1, COMPOUND I 50 mg is an administration group of the formulation prepared in Example 1, COMPOUND I 100 mg is an administration group of the formulation prepared in Example 2, and COMPOUND I 200 mg is an administration group of the two formulations prepared in Example 2.

2. Usage, Dose, and Administration Period

Drug Administration Schedule

The drug administration schedules of clinical trials carried out according to the present disclosure are shown in Table 2 below.

TABLE 2

|  | Period 1 | | | Period 2 | | Follow-up visit |
|---|---|---|---|---|---|---|
|  | −1 | 1 | 2 | 1 | 2 |  |
| Administration of trial drugs |  | X |  | Drug withdrawal period | X |  |  |
| Hospital admission | X | X | X |  | X | X |  |
| PK blood drawing |  | X | X |  | X | X |  |
| pH monitoring | X | X | X |  | X | X |  |
| Outpatient visit |  |  |  |  |  |  | X |

Administration Method

Trial drugs were administered between P.M. 08:30 and P.M 10:30 together with 200 mL of water in a state where water intake was restricted 1 hour before the administration of the trial drugs. Investigator has instructed the trial subjects to take the trial drugs, and has observed the oral cavities of the trial subjects whether all the trial drugs were well taken. The trial subjects were restricted not to lie down for 3 hours after the administration of the trial drugs, but were not restricted when they must lie down or be semi-reclined during a clinical test procedure (for example, electrocardiogram examination). The trial subjects were to take a proper posture if any abnormal reaction occurs at any point.

Food and Water Intake pH sensor (PH probe) insertion started in a state where the trial subjects can freely take water until 1 hour before the insertion of a pH sensor (PH probe) but do not take water thereafter.

The trial subjects were allowed to take a small amount of water (150 mL or less) in order to insert a pH sensor easily. The intake of drinking water and food was prohibited for 4 hours after the insertion of a pH sensor, and, particularly, the intake of water was restricted for 4 hours after the administration of the trial drugs (On the day before the administration (−1 D), for 4 hours after estimated drug administration time). After the trial subjects woke up next day, a small amount of water (about 50 mL) was provided to the trial subjects at 2 hour intervals during 12 to 24 hours after the administration of the trial drugs (On the day before the administration (−1 D), during 12 to 24 hours after estimated drug administration time), and the intake of water was not restricted during meal time. Meanwhile, standard meal was provided in the form of liquid meal or semi-liquid, and dinner was finished at least 3 hours before drug administration time (On the day before the administration (−1 D), estimated drug administration time). After dinner, an empty stomach state was maintained until breakfast next morning.

Prohibition of Administration in Combination with Other Drugs

Except when permitted by the investigator, trial subjects were regulated not to take medications including other trial drugs or herbal products during the period from when the subject screening started until when final safety evaluation was completed, and were regulated to first consult a investigator when expert-the-counter drugs, over-the-counter drugs, or oriental medicines are required to be used for therapeutic purposes due to occurrence of symptoms.

When the trial subjects needed medication other than that specified in this plan, the investigator was required to determine whether the trial subjects continuously participate in clinical trial or stops clinical trial, in consideration of pharmacological and pharmacokinetic (PK) characteristics of the medication, administration time of the medication, and the like. All medications taken by the test subjects during the trial were recorded.

3. Evaluation of Pharmacokinetic Parameters

Severe abnormal reactions did not occur during this clinical trial, and there were no mid-dropout subjects due to the abnormal reactions. Pharmacokinetic parameters on gastric pH were measured. The measured pharmacokinetic parameters are summarized in Table 3.

TABLE 3

| | |
|---|---|
| Time maintained at pH > 4 (Time pH > 4) | Duration of the time for which gastric pH exceed 4 during the gastric pH observation period |
| Time maintained at pH > 6 (Time pH > 6) | Duration of the time for which gastric pH exceed 6 during the gastric pH observation period |
| Integrated acidity | Acid concentration (mM) is calculated by $1000 \times 10^{-pH}$. Integrated acidity is time-weighted mean of acid concentrations represented by mmol · hr/L. Integrated acidity corresponds to area under the acid concentration-time curve from time zero to the last time point. |
| Percentage of inhibition of integrated acidity | This is calculated by 100 × ((baseline integrated acidity − treatment integrated acidity)/baseline integrated acidity) |
| Percentage of time of inhibition of gastric pH ≤ 4 | Time maintained at gastric pH ≤ 4 is calculated by 100 − percentage of time maintained at gastric pH > 4. Percentage of time of inhibition of gastric pH ≤ 4 is calculated by 100 × ((baseline time of gastric pH ≤ 4 − treatment time of gastric pH ≤ 4)/baseline time of gastric pH ≤ 4). |
| Median pH | Median pH during the gastric pH observation period |

Specifically, for the analysis of pharmacokinetic parameters, the changes of average 15-min median gastric pH over time were monitored. The main pharmacokinetic parameters set forth above were calculated using the data of total 24 persons obtained by the monitoring of gastric pH. The time function of pharmacokinetic parameters was schematically was illustrated to calculate the pharmacokinetic parameters, and these pharmacokinetic parameters were summarized using descriptive statistics (arithmetic mean (mean), standard deviation (SD), coefficient of variation (CV (%)), sample size (N), minimum value (min), maximum value (max), and median value (median)).

Meanwhile, the monitoring of gastric pH was carried out as fellows.

Period 1: for each examination period, 24 h for −1 D (before administration), 24 h for each of 1 D and 7 D (after administration)

Period 2: 24 h for 1 D (after administration)

TABLE 4

Evaluation of pharmacokinetic parameters after the administration of formulation (Compound I 50 mg) of Example 1

| PD parameters | 24 hours | | Night-time (0-12 hours) | | Day-time (12-24 hours) | |
|---|---|---|---|---|---|---|
| | Baseline (N = 12) | Post-dose (N = 12) | Baseline (N = 12) | Post-dose (N = 12) | Baseline (N = 12) | Post-dose (N = 12) |
| Time pH > 4 (%) | 13.33 (9.80) | 58.55 (19.41) | 8.48 (5.38) | 65.11 (21.13) | 17.85 (16.60) | 52.06 (27.17) |
| Time pH > 6 (%) | 1.84 (1.79) | 25.97 (19.69) | 2.16 (1.88) | 30.41 (24.00) | 1.50 (2.20) | 21.56 (25.37) |
| IA | 2131.79 (832.36) | 355.02 (289.99) | 1415.43 (616.79) | 170.73 (142.90) | 716.36 (431.07) | 184.29 (195.96) |
| % inhibition of IA | — | 78.18 (26.97) | — | 83.98 (17.58) | — | 62.64 (58.36) |
| % inhibition of Time pH < 4 | — | 51.35 (24.95) | — | 61.41 (24.16) | — | 39.65 (38.18) |
| Median pH | 1.34 (0.59) | 4.57 (1.25) | 1.00 (0.24) | 4.98 (1.23) | 1.86 (1.05) | 4.08 (1.67) |

Data were shown as arithmetic mean (SD).

TABLE 5

Evaluation of pharmacokinetic parameters after the administration of formulation (Compound I 100 mg) of Example 2

| PD parameters | 24 hours | | Night-time (0-12 hours) | | Day-time (12-24 hours) | |
|---|---|---|---|---|---|---|
| | Baseline (N = 12) | Post-dose (N = 12) | Baseline (N = 12) | Post-dose (N = 12) | Baseline (N = 12) | Post-dose (N = 12) |
| Time pH > 4 (%) | 13.12 (9.92) | 70.07 (18.31) | 9.76 (10.21) | 65.61 (20.83) | 15.91 (14.60) | 74.57 (20.20) |
| Time pH > 6 (%) | 3.49 (3.52) | 31.91 (16.37) | 4.44 (5.99) | 33.85 (19.04) | 2.48 (3.42) | 30.10 (23.69) |
| IA | 2181.43 (737.15) | 229.60 (188.76) | 1523.04 (591.59) | 161.88 (138.33) | 658.38 (233.62) | 67.72 (142.89) |
| % inhibition of IA | — | 88.78 (9.80) | — | 88.68 (9.14) | — | 90.74 (18.18) |
| % inhibition of Time pH < 4 | — | 66.22 (18.04) | — | 62.53 (20.93) | — | 71.47 (21.27) |
| Median pH | 1.29 (0.58) | 5.10 (1.07) | 0.99 (0.29) | 5.01 (1.33) | 1.77 (0.80) | 5.10 (0.96) |

Data were shown as arithmetic mean (SD).

TABLE 6

Evaluation of pharmacokinetic parameters after the administration of two formulations (Compound I 200 mg) of Example 2

| PD parameters | 24 hours | | Night-time (0-12 hours) | | Day-time (12-24 hours) | |
|---|---|---|---|---|---|---|
| | Baseline (N = 12) | Post-dose (N = 12) | Baseline (N = 12) | Post-dose (N = 12) | Baseline (N = 12) | Post-dose (N = 12) |
| Time pH > 4 (%) | 14.09 (8.15) | 81.73 (8.29) | 8.54 (4.53) | 78.15 (9.21) | 19.35 (16.13) | 85.34 (18.14) |
| Time pH > 6 (%) | 3.72 (3.55) | 48.44 (15.39) | 3.39 (2.74) | 53.63 (18.78) | 3.97 (4.80) | 43.29 (17.50) |
| IA | 2190.57 (989.48) | 141.62 (87.77) | 1390.22 (615.61) | 116.11 (66.35) | 800.35 (473.10) | 25.51 (55.42) |
| % inhibition of IA | — | 93.45 (3.47) | — | 91.17 (4.44) | — | 97.41 (5.33) |
| % inhibition of Time pH < 4 | — | 78.87 (8.73) | — | 76.00 (10.41) | — | 82.48 (19.71) |
| Median pH | 1.13 (0.23) | 5.90 (0.49) | 0.98 (0.18) | 6.00 (0.44) | 1.91 (1.05) | 5.62 (0.75) |

Data were shown as arithmetic mean (SD).

TABLE 7

Evaluation of pharmacokinetic parameters after the administration of dexlansoprazole formulation (dexlansoprazole 60 mg) of Comparative Example

| PD parameters | 24 hours | | Night-time (0-12 hours) | | Day-time (12-24 hours) | |
|---|---|---|---|---|---|---|
| | Baseline (N = 12) | Post-dose (N = 12) | Baseline (N = 12) | Post-dose (N = 12) | Baseline (N = 12) | Post-dose (N = 12) |
| Time pH > 4 (%) | 13.36 (8.75) | 60.55 (5.86) | 9.79 (9.89) | 37.78 (11.08) | 16.89 (14.70) | 83.06 (8.87) |
| Time pH > 6 (%) | 3.56 (3.99) | 25.85 (14.82) | 4.32 (6.06) | 17.76 (9.11) | 2.80 (4.50) | 33.71 (24.70) |
| IA | 2268.28 (955.56) | 719.54 (243.09) | 1399.45 (562.46) | 696.55 (256.65) | 868.82 (519.84) | 22.89 (25.89) |
| % inhibition of IA | — | 64.66 (15.92) | — | 44.06 (25.77) | — | 97.01 (3.29) |
| % inhibition of Time pH < 4 | — | 53.96 (8.57) | — | 29.98 (15.62) | — | 79.80 (9.53) |
| Median pH | 1.13 (0.27) | 4.98 (0.60) | 1.02 (0.31) | 2.55 (1.16) | 1.73 (0.93) | 5.56 (0.63) |

Data were shown as arithmetic mean (SD).

From the results of evaluation of pharmacokinetic parameters, the administration group of the compound of Chemical Formula 1 according to the present disclosure exhibited a tendency to rapidly increase gastric pH, compared to the administration group of dexlansoprazole, which is a comparison group. That is, the average pH reached 4 or higher within 2 hours after the administration of all dose groups (50 mg, 100 mg, and 200 mg) of the compound of Chemical Formula 1, whereas pH first reached 4 or higher about 7 hours after the administration of dexlansoprazole.

Further, the gastric pH values of administration groups of the compound of Chemical Formula 1 according to the present disclosure show a dose-dependent change. That is, during the observation period of 24 hours, the percentage of time when gastric pH is above 4 out of the total observation period (herein after "time pH>4") was 58.55% in the 50 mg administration group, 70.07% in the 100 mg administration group, and 81.73% in the 200 mg administration group.

Particularly, when comparing the pharmacokinetic parameters among the different doses for the period until 12 hours at night-time, the 50 mg administration group and the 100 mg administration group are relatively similar to each other. That is, in the 50 mg administration group and in the 100 mg administration group, the percentages of time pH>4 were 65.11% and 65.61%, respectively, and the average integrated acidity (IA) values were 170.73 mmol·hr/L and 161.88 mmol·hr/L, respectively. However, in the 200 mg administration group, the percentage of time pH>4 was 73.15%, and the average integrated acidity (IA) value was 116.11 mmol·hr/L, and thus a tendency of obvious inhibition of gastric acidity was observed.

Further, when comparing the pharmacokinetic parameters among the different doses for the period from 12 hours to 24 hours at day-time, in the 50 mg administration group and the 100 mg administration group, the percentages of time pH>4 were 52.06% and 74.57%, respectively, and the average integrated acidity (IA) values were 184.29 mmol·hr/L and 67.72 mmol·hr/L, respectively, and thus a dose-dependent change was observed. In the 200 mg administration group, the percentage of time pH>4 was 85.34%, and the average integrated acidity (IA) value was 25.51 mmol·hr/L.

Meanwhile, in the case of the administration group of dexlansoprazole 60 mg, which is a comparison group, the average percentage of time pH>4 for 24 hours and the average percentage of time pH>6 were 60.55% and 25.85%, respectively, which were similar to that of the 50 mg administration group of the compound of Chemical Formula 1 according to the present disclosure, and the integrated acidity (IA) value was highest among all of the administration groups.

Particularly, when comparing the pharmacokinetic parameters for the period until 12 hours at night-time, in the administration group of dexlansoprazole 60 mg, the percentage of time pH>4 was 37.78% and the percentage of time pH>6 was 17.76%, which were lower than that of all the administration groups of the compound of Chemical Formula 1. Meanwhile, when comparing the pharmacokinetic parameters for the period from 12 hours to 24 hours at day-time, the percentage of time pH>4 was 83.05%, and the average IA value was 22.89 mmol·hr/L. It was observed that the increase of gastric pH value after drug administration starts later than that of the compound of Chemical Formula 1. Pharmacodynamic characteristics are exhibited to an extent similar to 200 mg of the compound of Chemical Formula 1 after 12 hours, and the overall average values for 24 hours are similar to 50 mg of the compound of Chemical Formula 1.

Summarizing the results of clinical trials, when the compound of Chemical Formula 1 was administered at night-time, in all dose groups, the average gastric pH reached 4 or higher within 2 hours after the administration. Thus, the average gastric pH of the administration group of the compound of Chemical Formula 1 tends to increase rapidly compared to that of the administration group of dexlansoprazole, in which the average gastric pH reached 4 or higher after 7 hours.

Further, when the pharmacokinetic parameters among administration groups for 24 hours were calculated and compared with each other, the administration group of dexlansoprazole 60 mg showed a generally similar pattern to the administration group of the compound 50 mg of Chemical Formula 1 according to the present disclosure, showed a gastric acid inhibition tendency lower than those of all the administration groups of the compound of Chemical Formula 1 according to the present disclosure during the period until 12 hours at night-time, and showed a similar tendency to the administration group of the compound 200 mg of Chemical Formula 1 according to the present disclosure during the period after 12 hours at day-time.

The invention claimed is:

1. A method for treating nocturnal acid breakthrough, comprising administering a pharmaceutical composition to a subject in need thereof, wherein the composition comprises a compound represented by Chemical Formula 1 or a pharmaceutically acceptable salt thereof, as an active ingredient, (Chemical Formula 1)

2. The method of claim 1, wherein the composition comprises 10 mg to 500 mg of the compound represented by Chemical Formula 1 or the pharmaceutically acceptable salt thereof.

3. A method for treating nocturnal acid breakthrough, comprising administering a unit dosage form to a subject in need thereof, wherein the unit dosage form comprises 10 mg to 500 mg of a compound represented by Chemical Formula 1 or a pharmaceutically acceptable salt thereof, (Chemical Formula 1)

4. The method of claim 3, wherein the unit dosage form further comprises a pharmaceutically acceptable carrier.

5. The method of claim 3, wherein the subject is a patient suffering from a disease selected from the group consisting of erosive gastroesophageal reflux disease (GERD), non-erosive gastroesophageal reflux disease (NERD), gastric ulcer, Barrett's esophagus, and esophagus motility disorder.

6. The method of claim 3, wherein the unit dosage form alleviates or ameliorates symptoms of heartburn.

7. The method of claim 3, wherein the unit dosage form is administered before dinner or bedtime.

8. The method of claim 3, wherein the unit dosage form is administered one to three times a day to a lowest acceptable daily dose.

9. The method of claim 3, wherein the unit dosage form is a unit dosage form for oral administration.

10. The method of claim 3, wherein the percentage of time when gastric pH is maintained at 4 or higher out of 12 hours after the administration of the unit dosage form is 65% or more.

11. The method of claim 3, wherein the gastric pH reaches 4 within 2 hours after the administration of the unit dosage form.

12. The method of claim 1, wherein the composition comprises 50 mg to 200 mg of the compound represented by Chemical Formula 1 or the pharmaceutically acceptable salt thereof.

13. The method of claim 3, wherein the unit dosage form comprises 50 mg to 200 mg of the compound represented by Chemical Formula 1 or the pharmaceutically acceptable salt thereof.

\* \* \* \* \*